April 30, 1963 R. D. MOORE Plant Pat. 2,257
CAMELLIA JAPONICA PLANT
Filed May 14, 1962
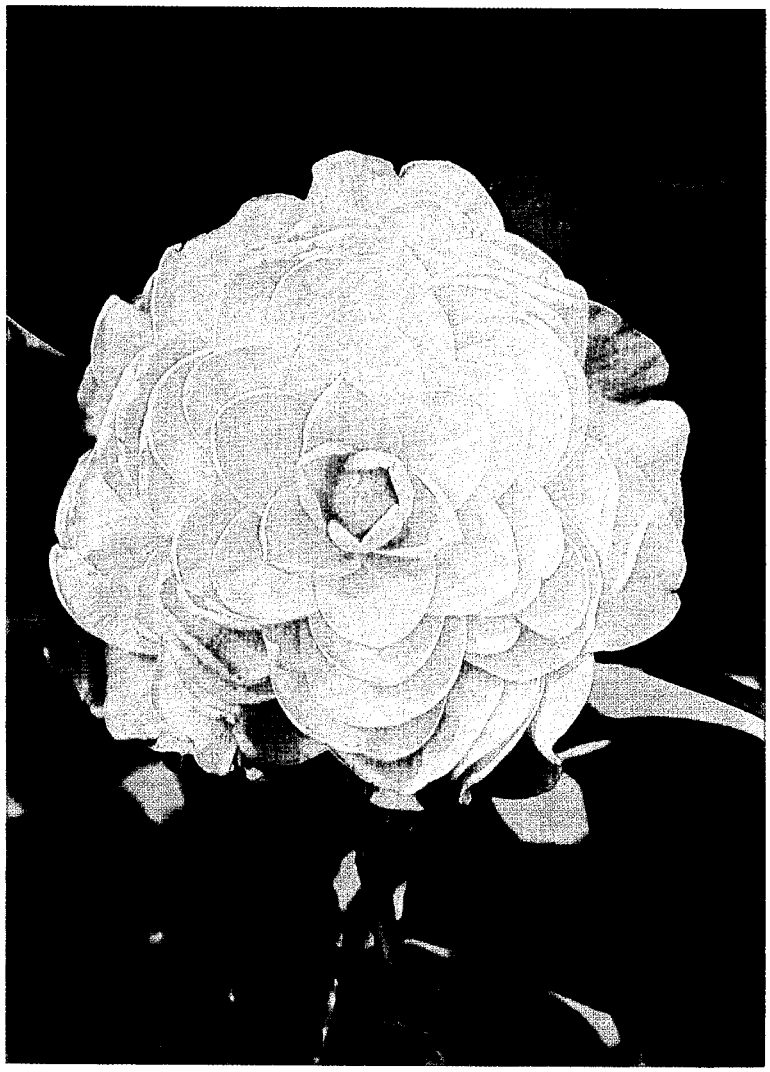
INVENTOR.
ROBERT D. MOORE
BY
J. F. Cuneo
ATTORNEY United States Patent Office Plant Pat. 2,257
Patented Apr. 30, 1963

2,257
*CAMELLIA JAPONICA* PLANT

Robert D. Moore, Glendora, Calif., assignor to Monrovia Nursery Company, Azusa, Calif., a corporation of California Filed May 14, 1962, Ser. No. 194,741
1 Claim. (Cl. 47—60)

The present invention relates to a new and distinct variety of camellia plant of the *japonica* species.

The new and distinct variety is characterized by its large formal double Neyron Rose flowers with thick broadly obovate outer petals, the tips of which are retuse, and the smaller inner petals that are broadly elliptic and involute, and for the strong adherence of the flowers to their receptacles, both while on the plant and as a cut flower; and by its vigorous, compact, upright habit and its large faintly serrated leaves.

The new variety was discovered by me as a chance seedling that grew in my cultivated property located at 15789 Union Avenue, Los Gatos, California, in 1956. The seed producing parent is *Camellia japonica* Pink Star, an unpatented variety; the pollen parent is unknown. The new plant does not resemble its seed parent *Camellia japonica* Pink Star in that the flower of the new variety is a large formal double and is Neyron Rose in color with the petals veined by a darker shade of Neyron Rose, while *Camellia japonica* Pink Star is semi double and is Rose Pink in color.

Asexual reproduction of my new variety by numerous cuttings and graftings, as performed by me at Los Gatos, California, show that the foregoing characteristics and distinctions are present in all descendants of the new variety of camellia and that these characteristics are transmitted through succeeding propagations, thereby establishing that the strain is true. The plant cannot be reproduced true from seed.

The accompanying illustration in full color, shows a typical group of the flowers and the vegetative growth of the new variety. This colored illustration is as correct as it is possible to reproduce the colors by this form of illustration. The colored photographic illustration was taken when the flowers on the plant were slightly past their peak condition, therefore the slight brown discoloration that is present at the ends of some of the petals would not be seen in a flower prior to or at its peak condition.

A detailed description of my new variety follows. To facilitate the identification of the important colors referred to in the specification, the color terminology adopted by the British Horticultural Colour Charts has been adopted.

*The Plant*

Parentage: Chance seedling.
*Seed parent.*—*Camellia japonica* Pink Star.
*Pollen parent.*—Unknown.

Form: Bush.
Growth habit: Vigorous, compact and upright.
Foliage:
*Quantity.*—Abundant.
*Size.*—Leaves are from 3⅝" to 3⅞" in length and from 2¼" to 2½" in width.
*Shape.*—Elliptic oblong, tip of leaf is acuminate, base of leaf is obtuse acute.
*Texture.*—Leathery. Smooth glossy upper side with a smooth underside.
*Color.*—Upper side of leaves is a dark glossy green. Underside of leaves is Parsley Green 0960/1.
*Ribs and veins.*—Ordinary.
*Edge of leaves.*—Faintly serrated.
Disease resistance: Generally similar to other varieties of *Camellia japonica.*
Wood: New wood has a bright green color. Old wood is greyish brown in color.

*The Flower*

Blooming habit: This variety is a so-called midseason bloomer with the usual flowering period extending from January to March in the coastal region of southern California.
Buds:
*Size.*—Large.
*Form.*—Pointed.
*Sepals.*—Smooth edged.
Bloom (when fully opened):
*Size.*—From 4" to 5" in diameter. Classed as large.
*Borne.*—Usually more than one on a stem. The stems are relatively short.
*Form.*—Formal double flower.
*Petalage.*—Imbricated—regular.
*Color.*—Neyron Rose 623/1 with the petals veined with Neyron Rose 623.
*Petals.*—Thick. Shape—outer petals are broadly obovate, with the tips retuse; inner petals are smaller in size and broadly elliptic and involute. Texture—the petals are of good substance.
Genital organs: None of the genital organs such as the stamens or pistils are usually visible due to the formal double nature of the flower.

I claim:

A new and distinct variety of camellia plant of the *japonica* species, substantially as herein shown and described, characterized particularly as to novelty by its large formal double, Neyron Rose flowers with thick, broadly obovate outer petals, the tips of which are retuse, and the smaller inner petals that are broadly elliptic and involute; by its vigorous, compact upright growth habit; and by its large, faintly serrated leaves.

No references cited.